(12) United States Patent
Heilman et al.

(10) Patent No.: US 9,137,987 B2
(45) Date of Patent: Sep. 22, 2015

(54) MODERATED RELEASE AQUATIC HERBICIDE FORMULATIONS

(75) Inventors: Mark A. Heilman, Carmel, IN (US);
Hamid Ullah, Whitakers, NC (US);
Tyler J. Koschnick, Westfield, IN (US)

(73) Assignee: SePro Corporation, Indianapolis, IN (US)

( * ) Notice: Subject to any disclaimer, the term of this patent is extended or adjusted under 35 U.S.C. 154(b) by 0 days.

(21) Appl. No.: 13/556,187

(22) Filed: Jul. 23, 2012

(65) Prior Publication Data

US 2013/0079227 A1 Mar. 28, 2013

Related U.S. Application Data

(60) Provisional application No. 61/510,947, filed on Jul. 22, 2011.

(51) Int. Cl.
| | | |
|---|---|---|
| *A01N 59/00* | (2006.01) |
| *A01N 43/00* | (2006.01) |
| *A01N 43/34* | (2006.01) |
| *A01N 43/36* | (2006.01) |
| *A01N 43/10* | (2006.01) |
| *A01N 33/00* | (2006.01) |
| *A01N 37/18* | (2006.01) |
| *A01N 47/28* | (2006.01) |
| *A01N 33/16* | (2006.01) |
| *A01N 35/00* | (2006.01) |
| *A01N 25/26* | (2006.01) |

(52) U.S. Cl.
CPC ..................... *A01N 25/26* (2013.01)

(58) Field of Classification Search
None
See application file for complete search history.

(56) References Cited

U.S. PATENT DOCUMENTS

| | | | | |
|---|---|---|---|---|
| 4,123,249 | A * | 10/1978 | Vartiak et al. | 504/152 |
| 4,277,364 | A * | 7/1981 | Shasha et al. | 504/250 |
| 4,353,962 | A * | 10/1982 | Himel et al. | 428/407 |
| 8,298,991 | B2 * | 10/2012 | Turner et al. | 504/128 |
| 2012/0021908 | A1 * | 1/2012 | Dunne et al. | 504/126 |

* cited by examiner

*Primary Examiner* — Alton Pryor
(74) *Attorney, Agent, or Firm* — Woodard, Emhardt, Moriarty, McNett & Henry LLP

(57) ABSTRACT

Described are preferred solid herbicidal formulations that include one or more herbicides in combination with a solid carrier, as well as methods of manufacture and use thereof. Solid herbicidal formulations are designed to deliver a moderated release of the incorporated load of herbicidal agent(s), for example to enhance uptake by target plants and/or the ability to spatially control a plant population within a body of water that exhibits flow.

41 Claims, 10 Drawing Sheets

MODERATED RELEASE AQUATIC HERBICIDE FORMULATIONS

REFERENCE TO RELATED APPLICATION

This application claims the benefit of U.S. Provisional Application No. 61/510,947, filed Jul. 22, 2011, entitled Moderated Release Aquatic Herbicide Formulations, which is hereby incorporated by reference in its entirety.

BACKGROUND

The present invention relates generally to the control of aquatic weeds, and in particular to solid-form aquatic herbicide compositions and their use in the control of aquatic weeds.

As further background, various methods exist for the control of aquatic weeds. The selection of an appropriate control method depends upon many factors such as environmental impact, cost effectiveness, efficacy, and the like. The various control methods available include physical controls such as mechanical harvesting, hand pulling or cutting, or the use of bottom barriers or water level draw-down. These methods can be both time consuming and labor intensive, and can create significant environmental disturbance, especially when considered on a large scale.

Biological controls such as the use of triploid grass carp can be desirable in some aquatic systems in that they reduce the use of equipment and have the potential for long term control of aquatic weeds. Nonetheless, in many aquatic systems, triploid grass carp often completely remove all aquatic vegetation for many years. The long-term environmental impacts result in reluctance of many natural resource managers to use triploid grass carp for these purposes. In temperate aquatic systems, the efficacy of such biological controls can also vary widely, and is dependent upon factors such as feeding preferences, metabolism, temperature, and stocking rate.

For these and other related reasons, the use of aquatic herbicides has become a common method for controlling invasive aquatic weeds. The use of herbicidal control nonetheless also presents risks and difficulties including the potential impact on the local environment, achieving an effective uptake of the herbicide by the target weeds, providing spatially-directed elimination of target weed populations, selectivity to non-target species, the potential for excessive decrease in the dissolved oxygen (DO) content of the waters due to rapid plant decay, and possible toxicity to other lifeforms.

In view of the background in this area, there are needs for improved and/or alternative aquatic herbicide formulations, and methods for their preparation and use. The present invention is addressed to these needs.

SUMMARY

In one aspect, the present invention relates to solid aquatic herbicidal compositions that incorporate one or more systemic herbicides, such as auxin mimic and/or acetolactate synthase (ALS) aquatic herbicides, and control the release thereof in a fashion that can enhance efficacy against target weeds as compared to corresponding immediate or rapid release formulations. In particular embodiments, granular or other solid aquatic herbicidal compositions of the invention are designed to release less than about 70% by weight of the auxin mimic, ALS inhibitor and/or other aquatic herbicide(s) upon continuous immersion in static distilled water at 25° C. for 24 hours. Such granular herbicidal formulations can include an outer polymeric coating that encapsulates a mineral-containing granule, preferably a granule containing both mineral and plant fiber materials, and/or can be effective to release at least about 90% of their incorporated auxin mimic, ALS inhibitor and/or other aquatic herbicide(s) upon continuous immersion in static distilled water for 288 hours, more preferably for 144 hours, at 25° C. Preferred auxin mimic herbicidal agents include triclopyr and/or 2,4-d, more preferably in amine salt form. Preferred ALS herbidical agents include penoxsulam, imazamox, bispyribac, and bensulfuron methyl. In certain embodiments, the granular herbicidal agent can exhibit the following release profile for the auxin mimic (AM), ALS inhibitor and/or other systemic herbicide(s) when immersed in static distilled water at 25° C.:

| Time after Immersion | Total Weight % Of Original Auxin Mimic (AM) Herbicide(s) Released ([total weight of released AM herbicide(s) at indicated time point divided by total original weight of AM herbicide(s)] multiplied by 100) |
|---|---|
| 4 hours | 10% to less than 30% |
| 1 Day | 20% to less than 70% |
| 3 Days | 50% to 100% |

Solid granular formulations having advantageous release profiles as specified herein can be used to provide for improved control of aquatic plants in many aquatic sites. These release profiles provide for a moderated delay in release which can be effective expose the plant to relatively high levels of the herbicide(s) during the first three days after application of the granular formulation, which coincides well with the pattern of the herbicidal uptake and translocation in commonly targeted aquatic weeds.

Additional aspects of the invention relate to methods for controlling aquatic weeds comprising applying to an aquatic environment including the weeds an effective amount of a moderated release granular herbicide product as described herein.

Still additional aspects of the invention relate to methods for preparing moderated release granular herbicidal products as described herein.

Additional embodiments as well as features and advantages of the invention will be apparent to those of ordinary skill in the art from the descriptions herein.

Figure 4:
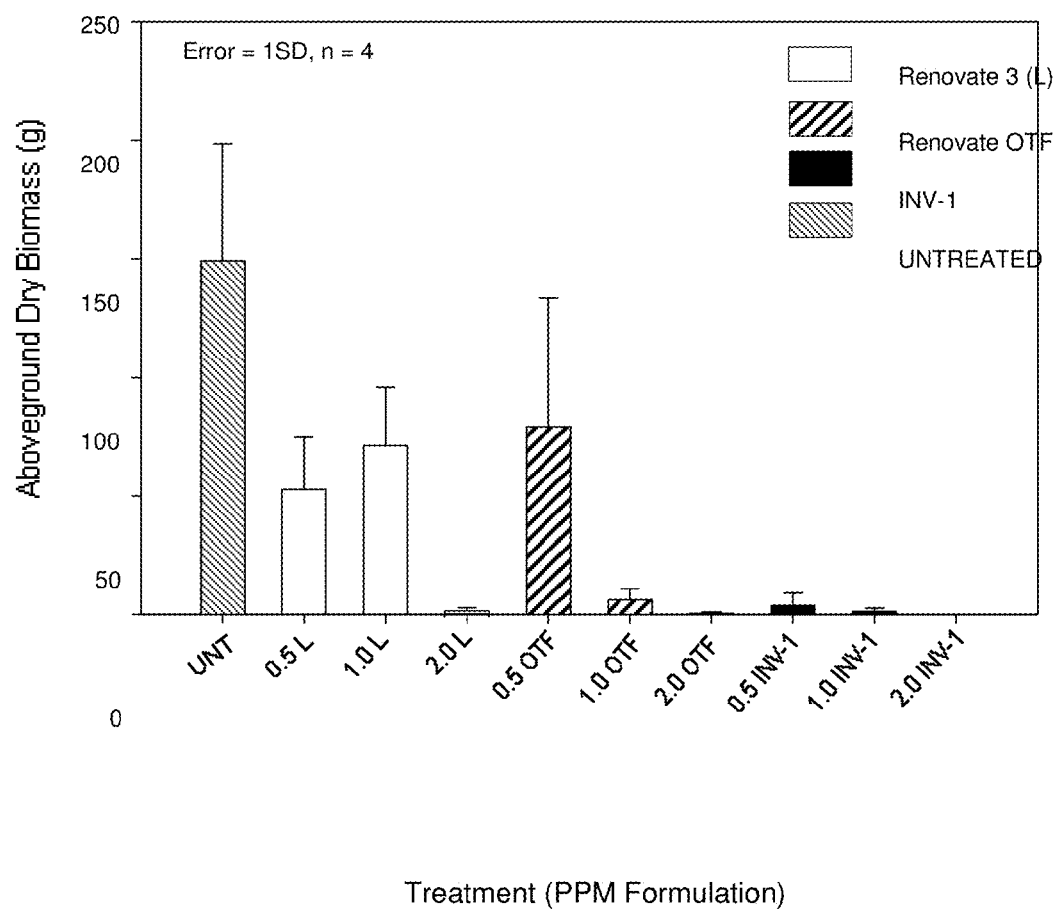

FIG. 4 shows control of control of established Eurasian watermilfoil at 6-weeks post treatment in 6700-L outdoor mesocosms using 3 different triclopyr formulations Renovate 3 liquid (3 lb ae triclopyr TEA), Renovate OTF granular uncoated Biodac with 10% triclopyr ae), and SP1468a granular (INV-1, 10% triclopyr ae with 4% latex overcoat). Various formulations applied at rates of 0.5, 1.0, and 2.0 ppm triclopyr ae. Mesocosm flow-through system resulted in 50% dilution every 5 hours.

Figure 5:
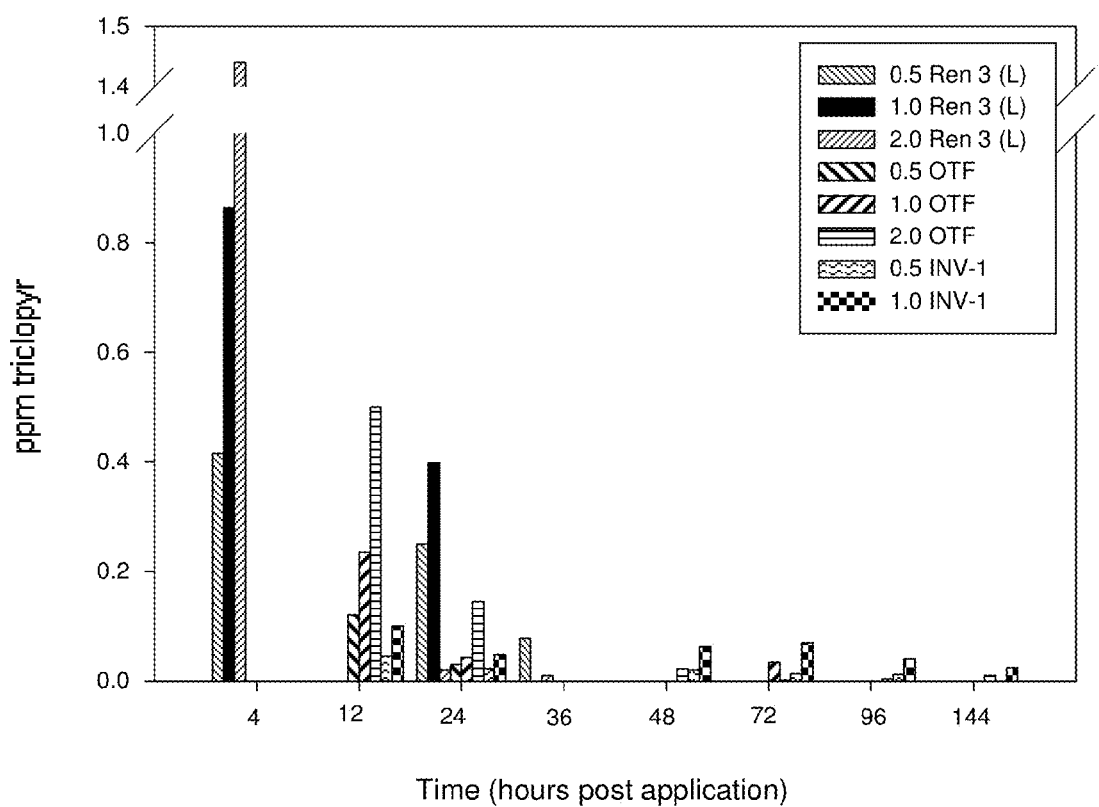

FIG. 5 shows triclopyr concentrations post application in 6700-L outdoor mesocosms using 3 different triclopyr granular formulations: Renovate 3 liquid, Renovate OTF, and INV-1 (biodac with 4% latex). The various formulations were applied at rates of 0.5, 1.0, and 2.0 ppm triclopyr.

Figure 6:
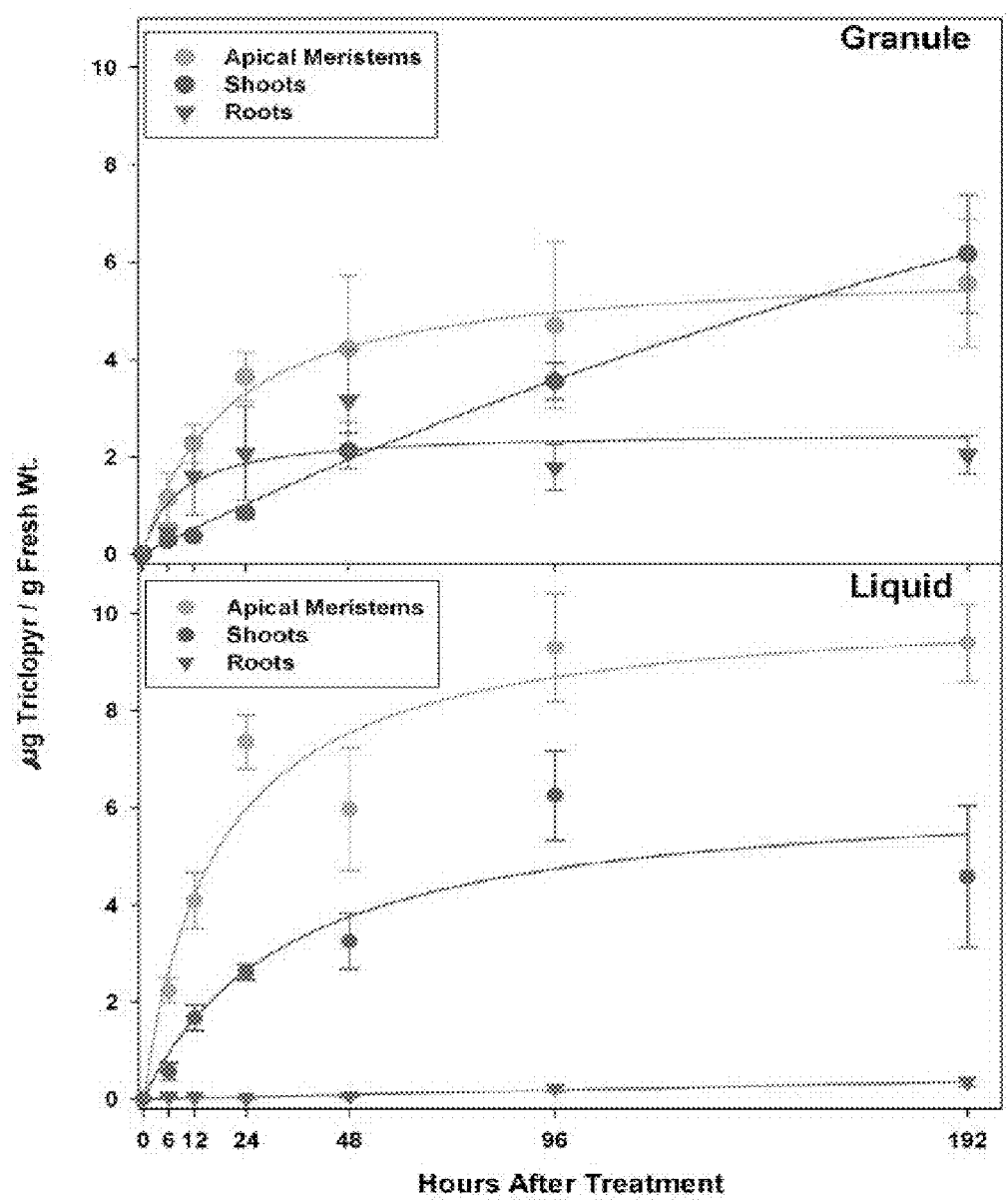

FIG. 6 shows triclopyr absorption by milfoil tissue section (apical meristem, shoot, root) at time intervals out to 192 hours following granular and liquid applications at 0.5 ppm triclopyr acid equivalent.

Figure 7:
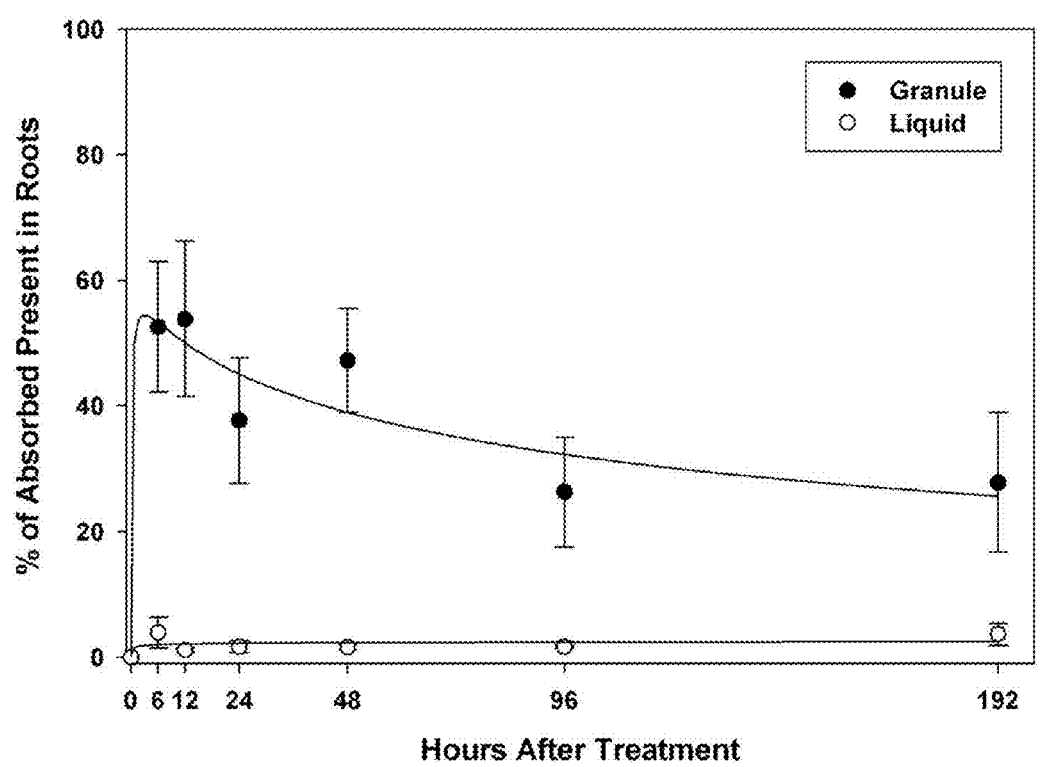

FIG. 7 shows triclopyr distribution in roots following granular and liquid applications at 0.5 ppm.

Figure 8:
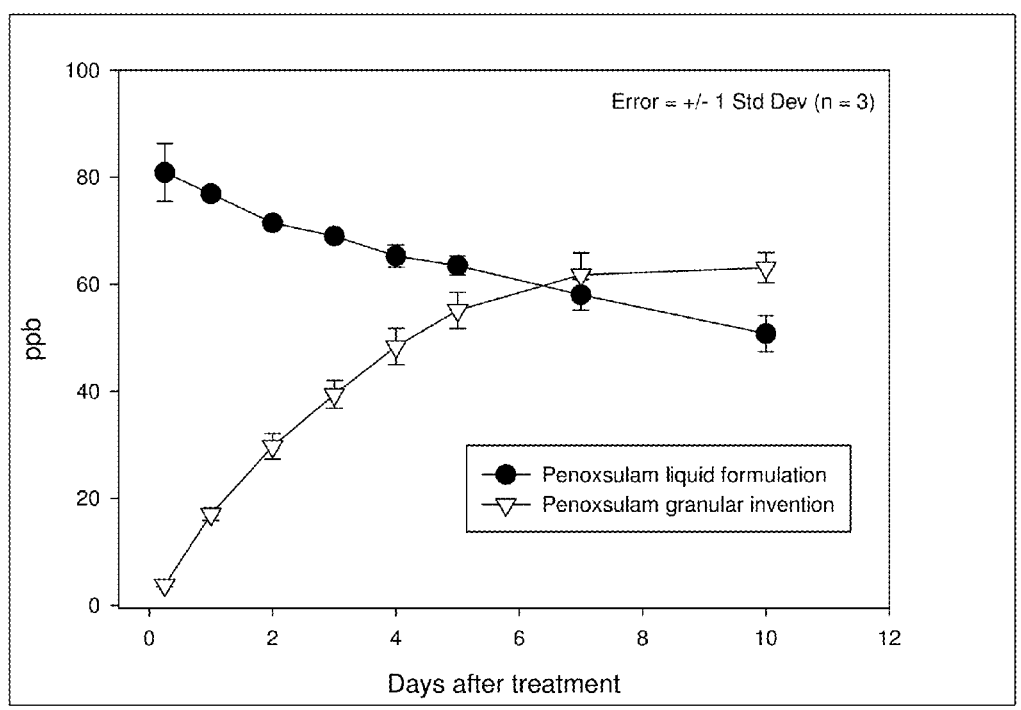

FIG. 8 shows penoxsulam herbicide concentration during the first 10 days following 90 ppb application of a liquid formulation of penoxsulam or a 2.7% active granular formulation of penoxsulam with 4.5% overcoat (invention) to water in 90-liter outdoor tanks containing pond sediment.

Figure 9:
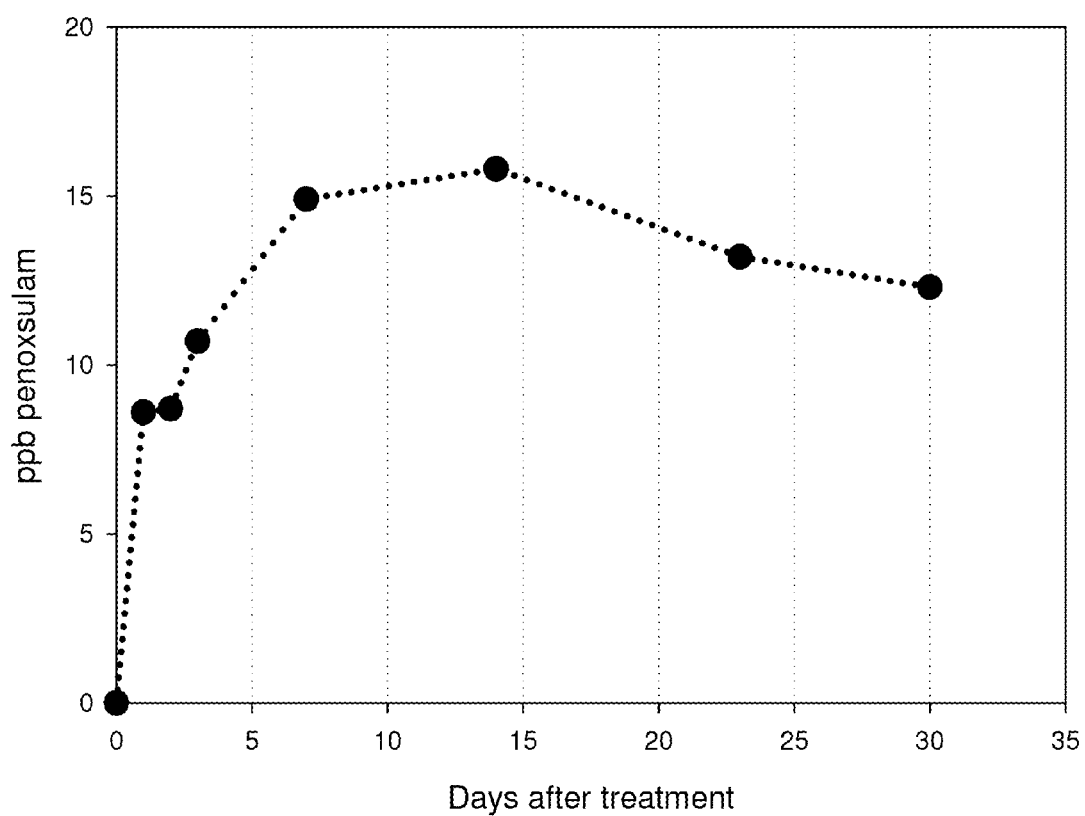

FIG. 9 shows penoxsulam herbicide concentrations in a 0.1-acre research pond through 30 days after application of a theoretical 20 ppb application of a 2.7% active granular formulation with 4.5% overcoat (invention).

Figure 10:
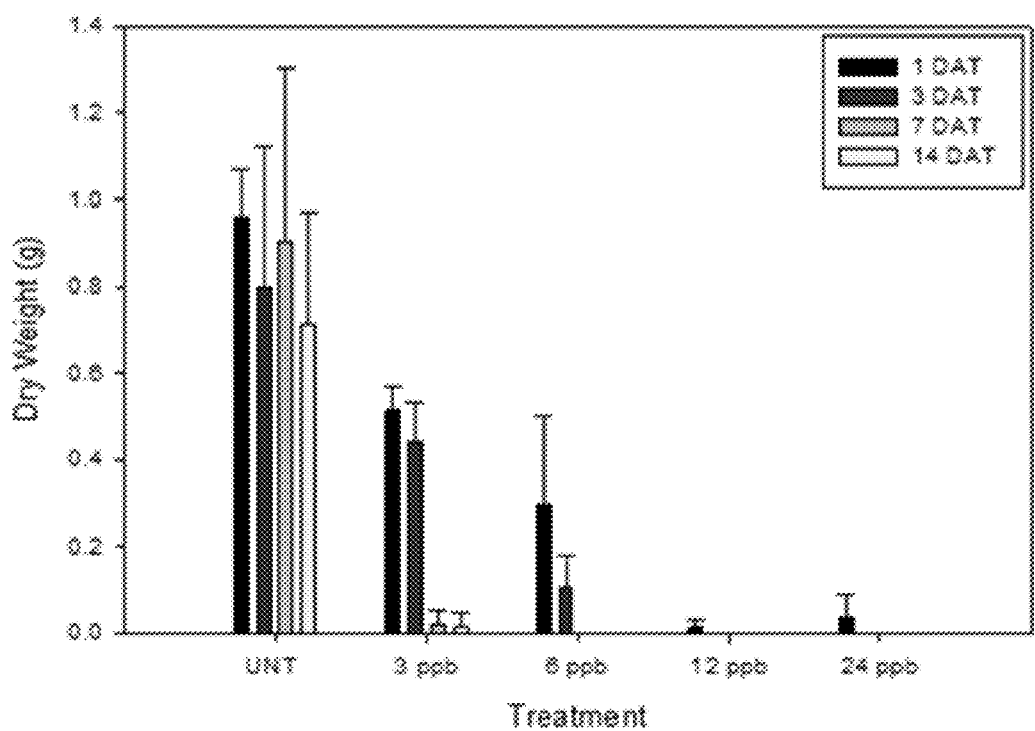

FIG. 10 shows dry aboveground biomass of curly-leaf pondweed after removal of penoxsulam exposures that lasted 1, 3, 7, or 14 days at rates of 3, 6, 12, or 24 ppb. Error bars are +1 standard deviation (n=3).

DETAILED DESCRIPTION

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

In certain preferred embodiments, the present disclosure provides herbicidal formulations loaded on a granule or other solid carrier useful for the control of aquatic plants, wherein the formulations include a systemic herbicide, such as an auxin mimic herbicide, such as 2,4-d or triclopyr, and/or an ALS herbicide such as penoxsulam, imazamox, bispyribac, or bensulfuron, loaded on a solid support. The present disclosure also provides methods for controlling aquatic plants which comprise introducing into a body of water having the plants an effective amount of an aquatic herbicide formulation of the invention, and methods for preparing aquatic herbicide formulations.

Herbicide compositions of certain embodiments of the invention will incorporate one or more auxin mimic herbicides. These herbicides act by mimicking the plant growth hormone auxin, causing uncontrolled and disorganized growth that leads to plant death. Auxin mimic aquatic herbicides in current, common aquatic use include, for example, 2,4-d and triclopyr. Combinations of 2,4-d and triclopyr as well as their combinations, individually or together, with other herbicides can also be used.

2,4-d and triclopyr herbicidal agents provide preferred agents for use in aspects of the invention. The chemical 2,4-d is formally known as 2,4-dichlorophenoxyacetic acid and is an herbicide in the phenoxyacetic acid family. Triclopyr is formally known as 3,5,6-trichloro-2-pyridyloxyacetic acid and is an herbicide in the picolinic acid family. Both 2,4-d and triclopyr herbicides are systemic agents used post-emergence for selective control of broadleaf weeds (dicots) and neither are effective against most grasses (monocots).

2,4-d dimethylamine salt formulation is one preferred product used in embodiments of the present disclosure, and is sold under the trade name DMA-4® or DMA-6® from Dow AgroSciences, Indianapolis, Ind., USA. 2,4-d dimethylamine salt is also a preferred form for aquatic use because it is substantially less toxic to other creatures, such as fish, than the butoxyethyl ester of 2,4-d (2,4-D Re-Registration Eligibility Decision, US Environmental Protection Agency, 2005). 2,4-d amine is more soluble in water than the water dispersible butoxyethyl ester form providing an increased mobility of the amine form in water and increasing the effectiveness of the treatment under several water quality conditions (e.g., higher alkalinity and pH). Nonetheless, ester, acid, amine, and other forms of 2,4-d may be used in aspects of the invention.

In an aquatic environment, 2,4-d herbicidal agents have good efficacy against various plant species including various milfoil species (*Myriophyllum* spp.) and water stargrass (*Heteranthera dubia*). At higher rates of applications, 2,4-d products are also effective against bladderwort (*Utricularia* spp.), white waterlily (*Nymphaea* spp.), spatterdock or yellow water lily (*Nuphar* spp.), water shield (*Brasenia* spp.), water chestnut (*Trapa natans*), coontail (*Ceratophyllum demersum*) and Marine eelgrass (*Zostera marina*). Spatterdock and coontail are often difficult to control and multiple treatments, separated by a period of time specified in the label or permit, may be necessary to achieve full control.

Some triclopyr products are registered for use in aquatic environments for control of emersed, submersed and floating aquatic plants in environments such as ponds, lakes, reservoirs, non-irrigation canals, seasonal irrigation waters and ditches which have little or no continuous outflow, marshes, and wetlands, including broadleaf and woody vegetation on banks and shores within or adjacent to these and other aquatic sites. Current commercial triclopyr products exist as the soluble triethylamine salt or the water dispersible butoxyethyl ester. Triclopyr triethylamine salt is the preferred form used in a number of embodiments of the present invention, and is sold under the trade name RENOVATE 3®, RENOVATE OTF®, AND RENOVATE LZR®, from SePRO Corporation, Carmel, Ind. Triclopyr triethylamine is preferred for aquatic use because it is substantially less toxic to creatures such as fish, than the butoxyethyl ester of triclopyr. Nonetheless, ester, acid, amine, and other forms of triclopyr may be used in aspects of the invention.

In an aquatic environment, triclopyr herbicidal agents are effective against such things as various milfoil species (*Myriophyllum* spp.), alligatorweed (*Alternanthera philoxeroides*), white waterlily (*Nymphaea* spp), spatterdock or yellow water lily (*Nuphar* spp.), water shield (*Brasenia* spp), american lotus (*Nelumbo lutea*), american frogbit (*Limnobium spongia*), aquatic soda apple (*Solanum tampicense*), pickerelweed (*Pontederia* spp.), purple loosestrife (*Lythrum salicaria*), water hyacinth (*Eichhornia crassipes*), water primrose (*Ludwigia* spp.), pennywort (*Hydrocotyle* spp.), parrotfeather (*Myriophyllum aquaticum*) and a variety of other plant species. Parrotfeather is often difficult to control and multiple treatments, separated by a period of time specified in the label or permit, may be necessary to achieve full control.

Three ALS herbicide chemistries are currently registered by US EPA as aquatic herbicides for in-water treatment of aquatic vegetation: penoxsulam (2-(2,2-difluoroethoxy)-6-(trifluoromethyl)-N-(5,8-dimethoxy[1,2,4]triazolo-[1,5c]pyrimidin-2-yl)-benzenesulfonamide), imazamox (2-[4,5-dihydro-4-methyl-4-(1-methylethyl)-5-oxo-1H-imidazol-2-yl]-5-(methoxymethyl)-3-pyridinecarboxylic acid), and bispyribac-sodium (or bispyribac) (sodium 2,6-bis[(4,6-dimethoxypyrimidin-2-yl)oxy]benzoate). Bensulfuron (Methyl 2-[(4,6-dimethoxypyrimidin-2-yl) carbamoylsulfamoylmethyl]benzoate) has been previously evaluated under US EPA Experimental Use Permit (EUP). Each ALS herbicide has a different spectrum in terms of activity on aquatic vegetation but target weeds in common to all include hydrilla (*Hydrilla verticillata*), Eurasian watermilfoil (*Myriophyllum spicatum*), water hyacinth (*Eichhornia crassipes*), and curlyleaf pondweed (*Potamogeton crispus*).

The present invention provides in certain aspects solid herbicidal compositions comprising one or more auxin mimic, ALS and/or other herbicidal agents, where the release of the agent(s) is controlled so as to retain the capacity to continue to deliver effective controlling levels of the agent(s) from the formulation over a period of more than a day (24 hours), more preferably more than two days (48 hours). Such formulations can provide continued delivery of the agent through an extended uptake period for the targeted plants, so that agent(s) activity thresholds can be established and maintained in the plants to enhance control.

In some embodiments, auxin mimic-loaded granular or other solid aquatic herbicidal compositions are provided that are effective to release less than about 70% by weight of the loaded auxin mimic, ALS and/or other aquatic herbicide(s) upon continuous immersion in static distilled water for 24 hours at typical use temperatures, for example at about 25° C. In preferred forms, these solid granular herbicidal compositions include an outer polymeric coating enclosing an inner granule or other particle, typically a mineral-containing granule or other particle. In some embodiments, these compositions can be effective to release at least about 90% of their incorporated auxin mimic, ALS and/or other aquatic herbicide(s) upon continuous immersion in static distilled water for 288 hours, more preferably 144 hours, at about 25° C. In addition or alternatively, these compositions can exhibit the release profile of Table 1 or Table 2 for the auxin mimic (AM), ALS and/or other herbicide(s) upon continuous immersion in static distilled water at 25° C.:

TABLE 1

| Time after Immersion | Total Weight % Of Original Herbicide(s) Released ([total weight of released herbicide(s) at indicated time point divided by total original weight of herbicide(s)] multiplied by 100) |
| --- | --- |
| 1 Day | 10% to less than 50% |
| 3 Days | 20% to less than 90% |
| 12 Days | 90% to 100% |

TABLE 2

| Time after Immersion | Total Weight % Of Original Herbicide(s) Released ([total weight of released herbicide(s) at indicated time point divided by total original weight of herbicide(s)] multiplied by 100) |
| --- | --- |
| 4 hours | 10% to less than 30% |
| 1 Day | 20% to less than 70% |
| 3 Days | 50% to 100% |

As disclosed, formulations of and used in the invention will be comprised of solid herbicide formulations. Such formulations may, for example, be in granular or powder form. Granular forms are preferred.

Preferred granular and other potential carriers will include, as at least a part thereof, a mineral carrier component. This mineral component may, for example, be filler's earth, sand, clays such as attapulgite clay, bentonite clays, or montmorillonite clay, vermiculite, perlite and other mineral-containing materials which absorb or which can be coated with the herbicidal compound(s).

In certain advantageous forms, the solid formulation includes a granulated carrier that includes a mineral component and plant fiber (e.g. paper). A preferred granulated carrier is commercially available under the tradename BIODAC® from Kadant GranTek Inc. of Green Bay, Wis., USA. BIODAC® granular carrier is an agglomerated carrier comprised of paper and clay. In particular, the BIODAC granular carrier includes paper fiber, Kaolin clay, and calcium carbonate. It is resistant to attrition, leaving its particle size distribution unaffected by transportation and application. BIODAC® granular carrier degrades into elements naturally occurring in the soil, and the carrier is made from recycled paper products or the waste generated by paper mills. BIODAC® granular carrier is available in standard particles sizes of 4/10 mesh, 10/30 mesh, 12/20 mesh, and 20/50 mesh (U.S Sieve Series). Another preferred carrier is commercially available under the tradename ECO GRANULE QD™ and ECO GRANULE HW™ from Cycle Group, Inc. of Mocksville, N.C., USA. ECO GRANULE QD™ or ECO GRANULE HW™ carrier is comprised of hardwood fibers, calcium carbonate and an organic binder, and is available in a 12/40 mesh particle size. For a tabulation of U.S. Sieve Series screen nomenclature, see Perry's Chemical Engineering Handbook, 7th Ed., McGraw-Hill, Inc., New York, N.Y. (1997), p. 19-20 (Table 19-6). The first number of the pair indicating the particle size is the mesh size where at least 95% of the granular particles pass through the mesh and the second number is the mesh size where no more than 5% of the granular particles pass through the mesh.

Methods of preparing agglomerated carriers including plant fiber such as cellulose and clay are disclosed, for example, in U.S. Pat. No. 4,560,527. A granulated carrier used in aspects of the present invention may also comprise cellulose fibers and mineral filler, and optionally an organic binder wherein each particle or granule of the carrier comprises a mixture of cellulose fibers and mineral filler, and optionally an organic or other binder material. In certain forms of the invention, the granular carrier is comprised of 10-90% of a plant fiber material and 10-90% of a mineral filler such as one or more clays or carbonates, and optionally about 1-10% organic binder, such as starch. More preferably, the carrier is comprised of about 20-50% plant fiber (especially cellulosic material) and about 80-50% of the mineral filler, and optionally about 1-10% binder. In another aspect, the carrier is comprised of about 30-50% plant fiber (especially cellulosic material) and about 70-50% of the mineral filler, and optionally about 1-10% binder. In other preferred aspects, the plant fiber/mineral carrier granules contain at least 30% by weight of cellulosic fibers.

In certain embodiments, the carrier granules or other solid particles of the herbicidal material have a density greater than water. In this manner, the granules or other particles have the capacity to sink when applied to an aquatic environment and will thus substantially avoid wind-driven or surface current-driven drift from the point of their application to a water body. As well, it is preferred that the granules or other particles have a density, shape and size such that they will break the surface tension of water when surface-applied to the water body, and thereafter sink.

In certain embodiments, the granular or other solid aquatic herbicide composition of the invention comprises from about 1% by weight to about 35% by weight of a triclopyr herbicidal agent, preferably an amine salt of triclopyr such as a triethylamine salt, more preferably about 20% to about 35% by weight of a triclopyr herbicidal agent, again preferably an amine salt of triclopyr such as a triethylamine salt. In this regard, unless otherwise indicated, all weight percents given herein are on a weight:weight basis. In other embodiments, the granular aquatic herbicide composition of the invention comprises from about 1% to about 35% by weight of a 2,4-d herbicidal agent, preferably an amine salt of 2,4-d such as a dimethylamine salt, more preferably from about 20% to about 35% by weight of a 2,4-d herbicidal agent, again preferably an amine salt of 2,4-d such as a dimethylamine salt. Granular formulations that are relatively highly loaded with the 2,4-d agent (preferably 2,4-d dimethylamine salt), triclopyr agent (preferably triclopyr triethylamine salt), or other auxin mimic or ALS herbicidal agent will be preferred, including those formulations loaded with at least 10% by weight of the auxin mimic or ALS or other herbicidal agent. In other embodiments, for example where the herbicidal agent is an ALS agent, the formulation can be loaded with about 0.5% to about 10% by weight of the herbicidal agent(s). The remainder of the weight of the compositions of the above formulations can in certain embodiments be constituted essentially from the carrier material, e.g. with the remainder constituted 90% to 100% by the carrier material in some embodiments. Additional materials that can be included in the composition include for example adjuvants such as surfactants, antifoam agents, and the like. Other active agents, such as additional herbicides, may also be included.

The herbicide(s) and potential other ingredients to be incorporated in the core of the formulation can be dissolved in a solvent such as water, organic solvents, or mixtures thereof, and applied to the mineral-containing or other core particle material, so as to coat and/or soak into the particle material. Agitation can be used to facilitate this loading process. The thus-loaded particulate material can then be partially or completely dried, depending upon the stage of manufacture and the nature of the final intended product. For solid formulations that will have an outer barrier coating, the thus-loaded particulate material can optionally be partially dried before application of the outer coating material.

In this regard, a latex or other polymeric coating can be applied to the solid particles of the herbicide formulation in any suitable manner, in order to slow the release of the auxin mimic herbicide(s) from the formulation. In certain modes, the polymeric coating is applied to the particles by applying a liquid preparation of polymeric coating material to the particles and then drying the preparation to form a polymeric film, desirably at least substantially continuous, that coats the particles. The granules or other solid particles can be agitated during the application of the liquid coating material and/or during the drying process, for example by tumbling in a rotating drum, agitation in a fluidized bed, or the like.

After the coating of the polymeric layer over the particles is completed, and the resulting coated product is dried, the polymeric layer can constitute from about 0.5% to about 10% by weight of the overall dried product, more preferably about 2% to about 7%, and in certain embodiments about 3% to about 6%. The polymeric layer can retard release of the auxin mimic herbicide(s) from the granule or other particle as compared to a corresponding uncoated granule or particle. In this regard, in some inventive variants the granule or particle is effective to release the auxin mimic herbicide(s) quite quickly but for the presence of the polymeric coating. Illustratively, a granule or other particle that, when uncoated, effectively releases at least 50% of the loaded auxin mimic herbicide(s) within 4 hours upon continuous immersion in distilled water at 25° C., can be coated as taught herein to exhibit one or more of the release profiles defined herein. This use of a relatively fast release granule or particle to ultimately achieve a moderate length release profile as disclosed herein has proven highly effective. Granulated carriers as disclosed herein that include a mineral component and a plant fiber (e.g. paper) component (e.g. BIODAC® granules) are preferred for these purposes.

Suitable liquid coating compositions for use in the present invention to coat the granules or other solid particles may include polymers and/or polymerizable monomers along with a liquid phase. The liquid phase can dissolve and/or suspend the polymers and/or monomers of the coating composition. Polymer latex coating compositions can be used with advantage, including aqueous latex coating compositions that are partially or completely acrylic latexes. In this regard, suitable aqueous acrylic latex compositions include those in the family of UCAR® latexes, available from Arkema Emulsion Systems, Cary, N.C., USA. UCAR® 651, which is an all acrylic latex having a glass transition temperature of 12° C., has been found advantageous in work to date. UCAR® 651 contains a butyl acrylate, methyl methacrylate, methacrylic acid polymer.

The mechanism of herbicide release from a polymer encapsulated granule or other particle with a continuous, defect-free coating, is believed to involve diffusion through the polymer layer. More specifically, the release can occur when water permeates from outside of the coated particle, through the polymer layer, and to the particle core containing the herbicide(s) distributed therein. Next, the water acts to dissolve or suspend a portion of the herbicide(s) to be released. Finally, the dissolved or suspended herbicide(s) permeate back through the polymer layer, to the outside of the encapsulated particle, where the herbicide(s) become available for uptake by the aquatic plants.

Accordingly, in particularly beneficial embodiments of the present invention, encapsulated granular or other solid particle herbicide compositions are provided, which use polymeric coating compositions to form complete and continuous polymer film coatings around the herbicide granules or other particles. The preferred coatings are durable and are not subject to coating attrition or breakdown under normal processing and handling conditions, and provide the final formulation as a free-flowing solid composition.

In use, the granular or other solid formulations of the invention will be applied to the body of water in sufficient amount to release and establish an effective level of the herbicide to control the target weed or weeds. In preferred forms the granular or other solid formulations will exhibit the capacity sink in water, and thus can be applied to or sink to the bottom of the body of water and generally remain there. In addition, it will be understood that release profile values given herein for the solid formulations when continuously immersed in distilled water at 25° C. can be and are expected to be essentially the same when they are applied to a body of water, such as a lake, pond, river, stream or other typical freshwater environment. Thus, the disclosed release profiles can be used in methods of treating bodies of water in accordance with the invention.

Typically, when using a granular composition incorporating a triclopyr herbicide as the sole herbicidally active agent, levels of triclopyr of about 0.05 ppm to about 2.5 ppm will be established in the treated water body. When using a granular composition incorporating a 2,4-d herbicide as the sole herbicidally active agent, levels of 2,4-d of about 0.1 ppm to about 4 ppm will be established in the treated water body. When using a granular composition incorporating both a triclopyr herbicide and a 2,4-d herbicide, levels of about 0.04 to 2.0 ppm and about 0.08 to 3.2 ppm, respectively, will be established in the water body. When using a granular composition incorporating penoxsulam or bensulfuron methyl, levels of about 0.003 to about 0.03 ppm will be established in the treated water body in accordance with some embodiments, and when using a granular composition incorporating bispyribac, levels of about 0.005 to about 0.06 ppm will be established in the treated water body in accordance with some embodiments. When using a granular composition incorporating imazamox, levels of about 0.01 to about 0.2 ppm will be established in the treated water body in accordance with some embodiments. Because aquatic plants also take up these and other auxin-mimic herbicides, ALS herbicides and/or other herbicides through their belowground roots, delivery of the herbicide(s) from granules or other particles that reside on and/or below the bottom surface of the water body is desirable. In this fashion, amounts of the herbicide(s) can be delivered to both above and below ground environments, to lead to uptake from both belowground and aboveground tissues of the plants. Particularly in respect of belowground delivery, this mode will make available herbicide(s) for uptake in a relatively static environment not subject to physical water movement (i.e., water currents) and dilution such as commonly experienced in shallow strata of the water column. Such flow conditions can remove the herbicide(s) from the treatment zone, which can both reduce the efficacy of the herbicide(s) on the target plants and enhance opportunity to move to and injure desired plants in other areas of the water body. Thus, an extended delivery of effective amounts of the herbicide(s) to the belowground environment for root uptake can assist in providing a more spatially-targeted elimination of an aquatic weed population, reducing the chance or extent of damage to desired aquatic plant species.

For the purpose of promoting a further understanding of embodiments of the invention as well as features and advantages thereof, the following specific Examples are provided. It will be understood that these Examples are illustrative, and not limiting, of the invention.

Example 1

Herbicide Uptake Study

Shoot Exposure

Eurasian watermilfoil or hydrilla apical fragments were collected from infested field sites and grown in topsoil cultures in greenhouse conditions until needed for uptake experiments. For uptake studies, 15 cm apical fragments were planted in glass jars in topsoil with a sand cap. Plants were allowed to grow in 30 L tanks until rooted (~14 days). Prior to experiments plants were removed from water and agarose gel (1.5%) was added to each sand cap surface in each jar to avoid root exposure. Three plants of each species were then placed in 4 L plastic containers containing 3 L of dechlorinated tap water. Plants were allowed to equilibrate overnight prior to treatment. During the study, plants were maintained at room temperature (25° C.) under grow lights. Six containers were treated for each experiment using the following aboveground (i.e., above gel layer and into shoot section) treatments of $^{14}$C-radiolabeled herbicide: Fluridone—10 ppb, Penoxsulam—10 ppb, Triclopyr—1,000 ppb (10 ppb $^{14}$C, remainder 'cold' material). All radiolabeled dosing of 10 ppb equated to 222,000 DPM of 14C herbicide. The selected total herbicide rates corresponded to typical use rates for these three aquatic herbicides. One study container of treated plants was harvested at 6, 12, 24, 48, 96, and 192 hours after treatment (HAT). Plants were separated into aboveground and belowground segments. Harvested plants were triple rinsed and dried for 48 hours at 60 C. After drying, plants were weighed and biomass recorded. Plants were then burned using a biological sample oxidizer and radioactivity quantified using liquid scintillation spectroscopy (LSS). All treatments were replicated three times and studies were repeated.

Figure 1A:
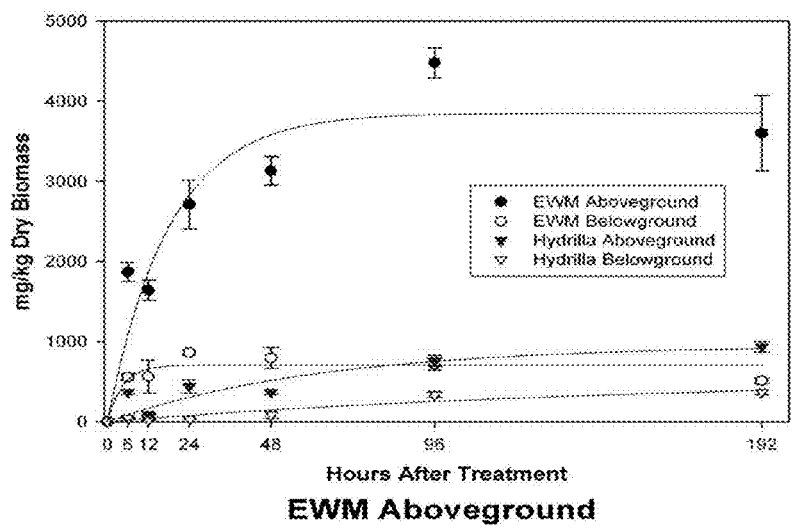
FIGS. 1A and 1B show a pattern of radiolabeled herbicide uptake and translocation to aboveground/belowground tissues following shoot exposure. Top (1A): Results for triclopyr on hydrilla and Eurasian milfoil showing maximum uptake by 96 hours. Bottom (1B): Greater dose-corrected uptake of triclopyr versus the herbicides fluridone and penoxsulam by Eurasian milfoil.
Figure 1B:
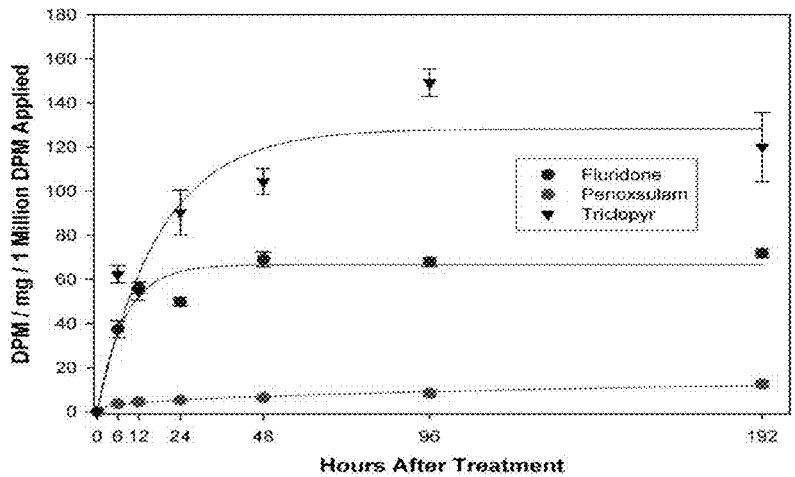

The results are shown in FIGS. 1A and 1B. Uptake of the auxin-mimic herbicide triclopyr in a shoot exposure produced faster translocation to belowground tissues than aboveground tissues (threshold levels reached in 6-12 hours for belowground versus 48-96 hours for aboveground, and maximum overall plant uptake within a 96-hour period (FIG. 1A). Maximum uptake is much greater on a dose-corrected basis for triclopyr than for two other herbicides tested (FIG. 1B).

Example 2

Herbicide Uptake Study

Root Exposure

Eurasian watermilfoil apical fragments were collected from infested field sites and grown in topsoil cultures in greenhouse conditions until needed for uptake experiments. 15 cm apical fragments were planted in glass jars in topsoil with a sand cap. Plants were allowed to grow in 30 L tanks until rooted (~14 days). Prior to experiments plants were removed from water and agarose gel (1.5%) was added to each sand cap surface in each jar to avoid root exposure. Three plants of each species were then placed in 4 L plastic containers containing 3 L of dechlorinated tap water. Prior to the experiment, plants were transplanted into glass jars filled with water plus a diluted growth media (Hoagland's Solution) and an eicosane wax plug was added to separate aboveground and belowground portions of the plant. Plants were allowed to equilibrate in this solution for 5 days. The root zone of each plant was treated with 200,000 dpm of 14C-triclopyr. Plants were then moved into 3 gallon tanks with other treated plants. Treatments were replicated 3 times and harvested at 12, 24, 48, 96, 192 HAT. Upon harvest, plants were separated into aboveground and belowground portions, dried, weighed and biomass recorded. Plants were then burned using a biological sample oxidizer and radioactivity quantified using liquid scintillation spectroscopy (LSS).

Figure 2:
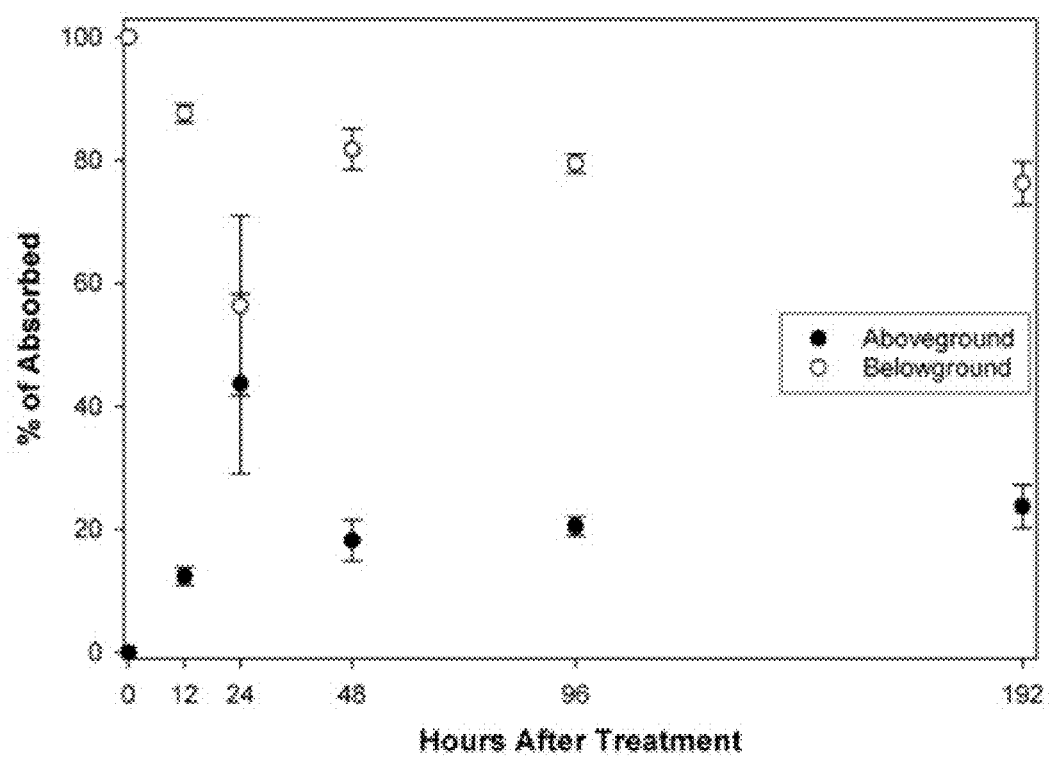
FIG. 2 shows uptake and percentage of radiolabeled herbicide detected in aboveground and belowground tissues of Eurasian milfoil through root exposure. Threshold absorption is reached within 12-24 hours for below ground tissue and near-maximum translocation to aboveground tissue is reached within 48 hours.

The results are shown in FIG. 2 and demonstrate that triclopyr is quickly taken up and translocated by Eurasian milfoil through root exposure with threshold uptake within 12-24 hours for belowground tissue and near-maximum translocation to aboveground tissue within 48 hours.

Example 3

Granular Versus Liquid Auxin Uptake

A study was conducted to directly compare spatially discrete uptake of 14C radiolabeled triclopyr by Eurasian milfoil delivered on a granular carrier versus a liquid formulation. 15 cm apical sections of Eurasian milfoil were planted in topsoil amended with slow-release fertilizer (Osmocote 14-14-14) and allowed to grow until they had reached a length of 50-75 cm, and produced several shoots. These plants were then clipped back to approximately 10 cm, and allowed to grow until they had produced ~50 cm of top growth. At this time, plants were potted in 3.75 cm round pots in sand amended with slow release fertilizer at 3 g/L. Following transplanting, plants were transferred to 36" tall 4.5" diameter acrylic tubes containing 7 L of water, and allowed to equilibrate overnight prior to herbicide treatment. 14C-triclopyr granules were formulated using Biodac™ carrier, Renovate 3 (3 lb ai per galleon triclopyr amine formulation), 14C-triclopyr, and distilled water to achieve a 1% triclopyr acid equivalent granular formulation. For granular treatments, 18 plants were treated with 350 mg (3.5 mg AE for an overall concentration of 0.5 ppm in the water column) of 14C-triclopyr granules containing 1,800,000 DPM of 14C-triclopyr. The granules were dropped through the water column and placed on the surface of the sand in study pots. For liquid treatments, 18 tubes were treated with 0.5 ppm triclopyr containing 1,500,000 DPM of 14C-triclopyr. During the studies, plants were maintained at room temperature under fluorescent grow lights. Plants were harvested at 6, 12, 24, 48, 96, and 192 hours after treatment. Three replicates were included for each of the time points, and both studies were repeated. At harvest, plants were removed from the treated water, triple rinsed and separated into three sections including apical meristems, shoots, and roots. Tissue samples were dried at 60 C for 48 h, and dry biomass recorded. Dried samples were oxidized using a Biological Sample Oxidizer, and radioactivity quantified using Liquid Scintillation Spectroscopy. Absorption was plotted and analyzed on a whole plant basis and by plant part. Translocation was analyzed and compared between the liquid and granular treatments. FIGS. 6 and 7 show distinctly different absorption profiles for granular and liquid formulations, particularly relative to root concentrations of herbicide (FIG. 7). Granular formulations lead to milfoil root concentrations many times higher than liquid formulation dosing of triclopyr herbicide that appears to equilibrate within the plant at 96 hours and beyond. Since milfoil root crown control is critical to achieving longer term control of this invasive plant with aquatic herbicide treatment, the improved control noted in mesocosm-scale efficacy testing with encapsulated granulars (e.g. INV-1 sample results reported herein) appears to be a function of the improved root exposures from granular delivery combined with more optimized herbicide exposure period from the invention.

Example 4

Preparation of Inventive Compositions

In this evaluation of prototype overcoated granular formulations, the triclopyr liquid herbicide formulation Renovate 3 (3 lb acid equivalent (ae) triclopyr triethanolamine liquid) was added to 4/10 mesh BIODAC dry carrier. The carrier was loaded at a rate to achieve a final herbicide concentration of 10% triclopyr acid as dry weight. The carrier and herbicide mixture was agitated in a customized laboratory agitator to ensure even uptake of herbicide by the carrier over a one-hour period. At that time, all liquid herbicide had been absorbed by the carrier.

Following preparation of this herbicide-loaded carrier, a liquid blend of UCAR® 651 latex (Arkema Emulsion Systems, Cary, N.C., USA) was added at ratios of 6.15%, 7.69%, or 9.20% in mixes with the herbicide-loaded carrier. The carrier and latex blends were agitated in a rotating drum agitator for one hour to ensure even coverage of the latex overcoat on the carrier. The final prototype overcoated materials were air dried on a tray-rack drying system to achieve final latex dry solid concentrations of 4% (INV-1), 5% (INV-2), and 6% (INV-3).

Example 5

Auxin Release Testing

Overcoated granular formulation prototypes INV-1, INV-2, and INV-3 were tested for triclopyr herbicide release characteristics versus uncoated granular formulation (Renovate OTF—commercial 10% triclopyr ae formulation). Four gallons of well water (Whitakers, N.C. research facility) were placed within 5-gallon containers. Container water was dosed with samples of overcoated granules INV-1, INV-2, or INV-3. A container dosed with OTF was also set up as a reference. All dosing was targeted at 5 ppm triclopyr ae but due to the small scale of the test relative to granular loading, variance of up to 20% from target was possible. Each container was sealed to prevent evaporation and placed in the dark (to prevent any possible triclopyr photolytic breakdown) at room temperature (25° C.). Water samples were taken from statically incubated containers at 4 hours and then 1, 3, 4, 5, and 6 days after start of the study. Water samples were analyzed for triclopyr content using a validated HPLC method.

Figure 3:
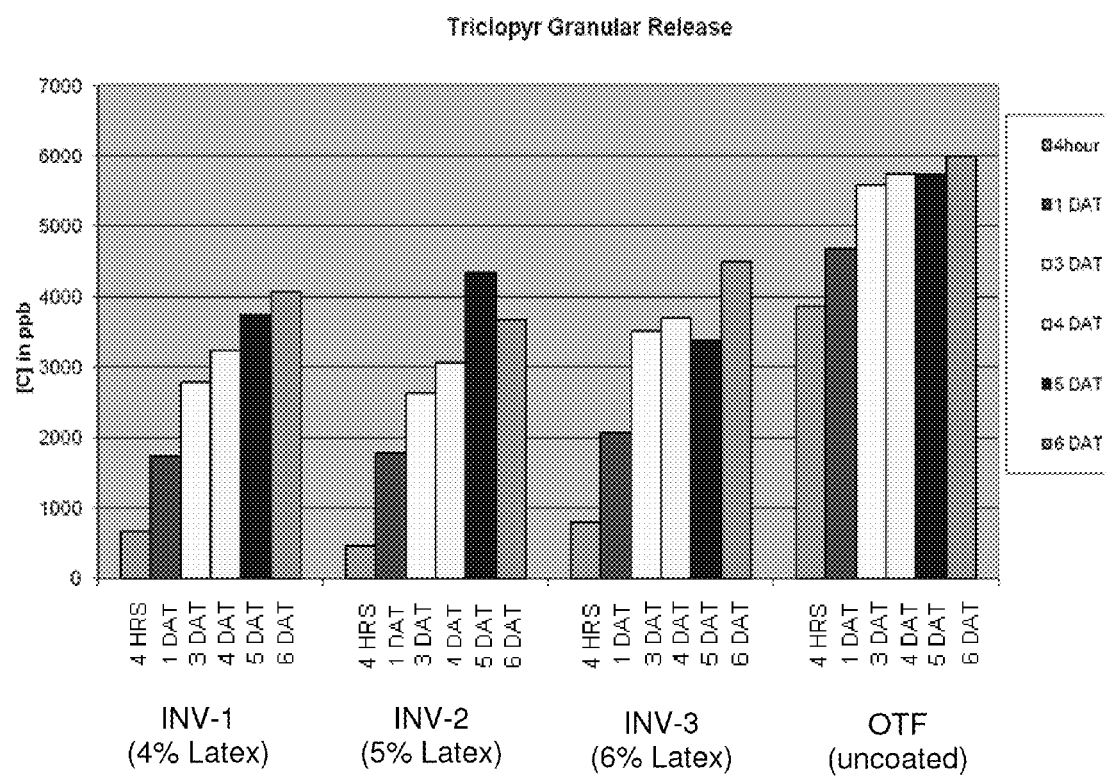
FIG. 3 shows release of triclopyr from Biodac carrier loaded with 10% triclopyr TEA and overcoated with 4% (INV-1), 5% (INV-2), or 6% (INV-3) latex. OTF formulation has no latex overcoating. Theoretical dosing was targeted at 5 ppm triclopyr but due to small-scale nature of both prototype production and release testing, actual dosing may have varied +/−20%.

The results are shown in FIG. 3. As demonstrated, through use of latex or other suitable granular overcoating technology, auxin-mimic herbicide release from a Biodac primary carrier can be slowed to a more effective period for targeted application. Latex overcoating was demonstrated to slow triclopyr release from a Biodac carrier material such that the herbicide releases over several days versus 4 to 6 hours for a corresponding uncoated formulation.

Example 6

Auxin Mesocosm Testing

A study using mature Eurasian water milfoil in 6700-L outdoor mesocosms was conducted to examine the performance and dissipation of three granular triclopyr formulations: liquid Renovate 3 (3 lb ae triclopyr TEA liquid), Renovate OTF (10% ae (acid equivalent) triclopyr TEA on Biodac, uncoated), and Formulation INV-1 of Example 3 (10% ae triclopyr TEA on Biodac with 4% latex overcoat). Mesocosms were equipped with flow through systems to exchange water fully in 5 hours (i.e., 50% product dilution every 5 hours). Water samples were collected for herbicide dissipation at 4, 24, 36, and 48 hours post application for Renovate 3-treated tanks and at 12, 24, 48, 96, and 144 hours. Triclopyr levels were quantified using an active-specific immunoassay method. At 6 weeks post application, aboveground biomass of treated milfoil was harvested, dried for 96 hours at 70 C, and weighed to determine control performance.

The results are shown in FIGS. 4 and 5. It was demonstrated that Formulation INV-1 achieved greatly improved control of the established milfoil at 6 weeks post treatment harvest (FIG. 4), and that Formulation INV-1 exhibited gradual extended triclopyr release for improved exposure (FIG. 5) versus both currently registered Renovate liquid and Renovate OTF granular formulations. These data evidence that the inventive moderate release formulations can be used to achieve enhanced results in aquatic weed control, including for example in the spatially targeted application of triclopyr and similar auxin mimic herbicides.

Example 7

ALS Release Testing and Related Hydrilla and Curly Leaf Pondweed Efficacy

Studies were conducted to document the rate of herbicide release rate from a 4.5% UCAR-651 latex coated Biodac formulation of the ALS herbicide penoxsulam. This formulation was designed similar to auxin formulations to provide a modified release profile to extend herbicide exposure period in higher exchange aquatic treatment sites. For release testing, either 1.2 g of the granular penoxsulam or 0.034 mL of a 21.8% penoxsulam liquid formulation were added to shallow outdoor tanks containing 90 liters of water and a 10-cm layer of organic pond sediment. The study was conducted in triplicate with water samples from each treated tank collected at 6 hours after application and then at 24 hour intervals for 10 days after application. Analysis of penoxsulam concentrations was performed via HPLC.

Results show notably different dissipation profiles for the liquid formulation of penoxsulam versus the invented granular formulation. 91% of the target dose was recovered at 6 hours after application of liquid penoxsulam, while 50% of target dose of the invented granular penoxsulam was not measured until greater than 4 days after application (FIG. 8). The declining concentrations of herbicide are the result of photolysis in the outdoor tanks.

An additional study was performed with the inventive, coated penoxsulam granular formulation described in this Example in a 0.1 acre research pond (mean depth 3.5 feet). 320 g of coated formulation was applied to the study pond, and penoxsulam levels were monitored through water sampling at 1, 2, 3, 7, 14, 23, 30 days after application. Results indicate a gradual increase in penoxsulam levels through gradual release of the herbicide during the first week after application (FIG. 9). Herbicide levels peak at 7-14 days after treatment and then begin to decline via slow photolysis.

The sustained dosing documented for the invented granular formulation of penoxsulam is relevant for management of two invasive submersed aquatic plants, hydrilla (*Hydrilla verticillata*) and curly-leaf pondweed (*Potamogeton crispus*). A combination of ALS herbicides with the contact aquatic herbicide endothall as described in United States Patent Application Publication 20090298693, published Dec. 3, 2009 is a currently a new successful operational technique for spatially-targeted hydrilla management. Table 3 below presents a reproduction of results from aquarium-scale studies presented in the original Table 2 from US Patent Application Publication 20090298693 and documents that combined exposures to penoxsulam and endothall in excess of six days provide improved hydrilla control over either herbicide alone. The 7+ day release profile of the inventive coated penoxsulam formulation matches well with the exposure periods needed for optimal control with the combination.

TABLE 3

Reproduction of Table 2 from U.S. patent application No. XXXX (Koschnick et al 2009) showing results of 12-L aquarium trials examining exposure requirements for hydrilla control with a combination of the ALS herbicides. Data are mean dry weights of hydrilla (n = 3) following various exposures to combinations of endothall and penoxsulam simultaneously applied or sequenced (e.g., endothall followed-by (f/b) penoxsulam). Means followed by different letter are significantly different at p = 0.05 according to least significant difference (LSD).

| TREATMENT (mg/L a.e.) | 3-d | 6-d | 12-d | 24-d | 48-d |
|---|---|---|---|---|---|
| CONTROL | 3.48ab | 4.20a | 3.81a | 4.53a | 4.63a |
| PENOXSULAM (0.02) | 4.01a | 3.97a | 3.68ab | 3.24ab | 2.41ab |
| ENDOTHALL (0.68) | 2.24b | 2.61ab | 2.72c | 2.14bc | 1.62b |
| PENOXSULAM + ENDOTHALL (0.02 + 0.68) | 2.06b | 1.15b | 1.83d | 0.11d | 0.39b |
| ENDOTHALL f/b PENOXSULAM (0.68 + 0.02) | — | 1.28b | 0e | 0.73cd | — |
| PENOXSULAM f/b ENDOTHALL (0.02 + 0.68) | — | 2.04b | 2.87bc | 1.61bcd | — |
| (LSD) | 1.70 | 1.62 | 0.83 | 1.79 | 2.92 |

Relative to control of invasive curly-leaf pondweed (or CLP), greenhouse studies of penoxsulam concentration and exposure requirements to achieve control of this species have documented that exposure periods of 3-7 days to 3-6 ppb penoxsulam can provide effective control. FIG. 10 presents results of a representative greenhouse trial of penoxsulam treatment of CLP. 13-cm diameter pots were filled with potting soil amended with Osmocote slow release fertilizer (14-14-14). Four apical CLP tips, harvested from a culture at the SRTC, were planted into each pot. A one-inch sand cap was placed over the potting soil and submersed into 54 gallon tubs to allow for grow-out. At 19 days after planting, the five tubs were treated with 0, 3, 6, 12, or 24 ppb penoxsulam. Three pots per treatment were pulled out and placed into a common grow-out tank at 1, 3, 7, and 14 days after treatment (DAT). Once the plants were allowed to grow out for 28 DAT the plants were harvested to determine aboveground dry weight (48 hours at 70° C.).

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for controlling a submersed aquatic weed in a water body, comprising:
   applying to the bottom of the water body a granular aquatic herbicide comprising a particulate carrier incorporating one or more systemic herbicidal agents, wherein the granular aquatic herbicide releases less than about 70% by weight of the one or more systemic herbicidal agents within 24 hours after said applying and at least about 90% by weight of the one or more systemic herbicidal agents within 288 hours after said applying, wherein said particles of the particulate carrier have a polymeric layer effective to retard release of the one or more systemic herbicidal agents from the particles, wherein said particles of the particulate carrier have a density greater than water, and wherein the one or more systemic herbicidal agents are exposed to and taken up by roots of the submersed aquatic weed, and then translocated to aboveground tissue of the submersed aquatic weed.

2. The method of claim 1, wherein the granular aquatic herbicide further exhibits the following release profile for the herbicidal agent(s) after said applying:

| Time after Applying | Total Weight % Of Original Herbicidal agent(s) Released ([total weight of released herbicidal agent(s) at indicated time point divided by total original weight of herbicidal agent(s)] multiplied by 100) |
| --- | --- |
| 4 hours | 10% to less than 30% |
| 1 Day | 20% to less than 70% |
| 3 Days | 50% to 100%. |

3. The method of claim 1, wherein the herbicidal agent(s) include triclopyr and/or 2,4-d.

4. The method of claim 1, wherein the herbicidal agent(s) include triclopyr.

5. The method of claim 1, wherein the herbicidal agent(s) include 2,4-d.

6. The method of claim 4, wherein the triclopyr comprises an amine salt form of triclopyr.

7. The method of claim 5, wherein the 2,4-d comprises an amine salt form of 2,4-d.

8. The method of claim 1, wherein the herbicidal agent(s) include triclopyr or 2,4-d.

9. The method of claim 8, wherein the polymeric layer comprises an acrylic latex polymer.

10. The method of claim 8, wherein the particles comprise agglomerated granules including plant fiber and mineral filler.

11. The method of claim 8, wherein, but for the polymeric layer, the particles would release at least 50% of the incorporated herbicide(s) within 4 hours after said applying.

12. The method of claim 1, wherein at least one said one or more herbicidal agent is present in an amount of at least 10% by weight of said granular aquatic herbicide.

13. A method according to claim 1, wherein the granular aquatic herbicide comprises at least one auxin mimic herbicidal agent or at least one ALS inhibitor herbicidal agent.

14. A method according to claim 13, wherein the aquatic weed is watermilfoil or *hydrilla*.

15. A method according to claim 14 wherein the one or more systemic herbicidal agents include at least one auxin mimic herbicidal agent taken up by roots of the aquatic weeds or at least one ALS inhibitor herbicidal agent taken up by roots of the aquatic weeds, and wherein the solid particulate carrier comprises mineral-containing particles.

16. The method according to claim 1, wherein the granular aquatic herbicide comprises at least one said one or more systemic herbicide of penoxsulam, imazamox, bispyribac, and bensulfuron methyl.

17. The method of claim 1, wherein the one or more herbicidal agents includes an ALS herbicidal agent present in an amount of about 0.5% to about 10% by weight of said composition.

18. A solid herbicide composition useful for controlling submersed aquatic weeds, comprising:
    a solid particulate carrier; and
    one or more systemic herbicidal agents;
    wherein the solid herbicide composition is effective in the release of less than about 70% by weight of the one or more herbicidal agents within 24 hours, and at least about 90% by weight of the one or more systemic herbicidal agents within 288 hours, upon continuous immersion in static distilled water at 25° C.;
    wherein particles of the particulate carrier have a polymeric layer effective to retard release of the one or more systemic herbicidal agents from the particles; and
    wherein the particles of the particulate carrier are sink when applied to an aquatic environment exposing the one or more systemic herbicidal agents to roots of the submersed aquatic weeds which are taken up by the roots of the aquatic weeds and then translated to aboveground tissue of the aquatic weeds.

19. The composition of claim 18, which exhibits the following release profile for the herbicidal agent(s) upon continuous immersion in static distilled water at 25° C.:

| Time after Immersion | Total Weight % Of Original Herbicidal agent(s) Released ([total weight of released herbicidal agent(s) at indicated time point divided by total original weight of herbicide(s)] multiplied by 100) |
| --- | --- |
| 4 hours | 10% to less than 30% |
| 1 Day | 20% to less than 70% |
| 3 Days | 50% to 100%. |

20. The composition of claim 18, wherein the herbicidal agent(s) include triclopyr and/or 2,4-d.

21. The composition of claim 18, wherein the herbicidal agent(s) include a triclopyr agent.

22. The composition of claim 18, wherein the herbicidal agent(s) include a 2,4-d agent.

23. The composition of claim 16, wherein the triclopyr agent comprises an amine salt form of triclopyr.

24. The composition of claim 22, wherein the 2,4-d agent comprises an amine salt form of 2,4-d.

25. The composition of claim 18, wherein the particles comprise mineral-containing granules coated with the polymeric layer.

26. The composition of claim 25, wherein the polymeric layer comprises an acrylic latex polymer.

27. The composition of claim 25, wherein the mineral-containing granules comprise agglomerated granules including plant fiber and mineral filler.

28. The composition of claim 25, wherein, but for the polymeric layer, the granules would release at least 50% of the incorporated herbicide(s) within 4 hours upon continuous immersion in static distilled water at 25° C.

29. The composition of claim 18, wherein at least one said one or more herbicidal agent is present in an amount of at least 10% by weight of said solid herbicide composition.

30. A composition according to claim 18, wherein the solid aquatic herbicide comprises at least one auxin mimic herbicidal agent.

31. The composition of claim 18, wherein the at least one said one or more herbicidal agent includes an ALS herbicidal agent present in an amount of about 0.5% to about 10% by weight of said solid herbicide composition.

32. The composition according to claim 18, wherein the one or more systemic herbicidal agents comprise at least one of penoxsulam, imazamox, bispyribac, and bensulfuron methyl.

33. A solid herbicide composition useful for controlling submersed aquatic weeds, comprising:
 a particulate carrier comprising mineral-containing particles;
 one or more systemic herbicidal agents incorporated in said mineral-containing particles;
 said mineral-containing particles having a polymeric coating effective in the retard release of the systemic herbicidal agent(s) from the particles;
 wherein the composition is effective to release of less than about 70% by weight of the one or more herbicidal agents within 24 hours upon continuous immersion in static distilled water at 25° C.; and
 wherein the mineral-containing particles are sink when applied to an aquatic environment, exposing the one or more systemic herbicidal agents to roots of the weeds which are taken up by the roots of the aquatic weeds and then tracslated to aboveground tissue of the weeds.

34. The composition of claim 33, wherein said polymeric coating comprises a latex polymer coating.

35. The composition of claim 33, wherein the one or more herbicidal agents include a triclopyr agent.

36. The composition of claim 33, wherein the one or more herbicidal agents include a 2,4-d agent.

37. The composition of claim 33, wherein the one or more systemic herbicidal agents includes an auxin mimic herbicidal agent.

38. The composition of claim 33, wherein the composition is effective to release least about 90% by weight of the one or more herbicidal agents within 288 hours upon continuous immersion in static distilled water at 25° C.

39. The composition of claim 33, which exhibits the following release profile for the one or more herbicidal agents upon continuous immersion in static distilled water at 25° C.:

| Time after Immersion | Total Weight % Of Original Herbicidal agent(s) Released ([total weight of released herbicide(s) at indicated time point divided by total original weight of herbicide(s)] multiplied by 100) |
| --- | --- |
| 4 hours | 10% to less than 30% |
| 1 Day | 20% to less than 70% |
| 3 Days | 50% to 100%. |

40. The composition of claim 33, wherein, but for the polymeric coating, the granules would release at least 50% of the incorporated herbicide(s) within 4 hours upon continuous immersion in static distilled water at 25° C.

41. A method for making a solid herbicide composition useful in the control of aquatic weeds, comprising:
 incorporating one or more systemic herbicidal agents in a solid particulate carrier; and
 coating particles of said carrier with a polymeric coating that retards release of the one or more herbicidal agents from the carrier so as to prepare a particulate solid herbicide composition that is effective to release less than about 70% by weight of the one or more herbicidal agents within 24 hours upon continuous immersion in static distilled water at 25° C., wherein particles of the particulate solid herbicidal composition are sink when applied to an aquatic environment, exposing the one or more systemic herbicidal agents to roots of the weeds which are taken up by the roots of the aquatic weeds and then translated to aboveground tissue of the weeds.

\* \* \* \* \*